(12) United States Patent
Stevens et al.

(10) Patent No.: US 7,395,217 B1
(45) Date of Patent: Jul. 1, 2008

(54) WORKERS COMPENSATION INFORMATION PROCESSING SYSTEM

(75) Inventors: John R. Stevens, San Francisco, CA (US); Sheryl Lee Wilson, Walnut Creek, CA (US)

(73) Assignee: P2P Link, LLC, Farmington, CT (US)

( * ) Notice: Subject to any disclaimer, the term of this patent is extended or adjusted under 35 U.S.C. 154(b) by 0 days.

(21) Appl. No.: 09/506,432

(22) Filed: Feb. 17, 2000

(51) Int. Cl.
*G06Q 40/00* (2006.01)

(52) U.S. Cl. ............................................. 705/4; 705/2

(58) Field of Classification Search .................. 705/2–4
See application file for complete search history.

(56) References Cited

U.S. PATENT DOCUMENTS

| | | | |
|---|---|---|---|
| 4,916,611 A | | 4/1990 | Doyle, Jr. et al. |
| 4,987,538 A | * | 1/1991 | Johnson et al. ................ 705/2 |
| 5,070,452 A | | 12/1991 | Doyle, Jr. et al. |
| 5,182,705 A | * | 1/1993 | Barr et al. ..................... 705/11 |
| 5,544,044 A | * | 8/1996 | Leatherman ................... 705/3 |
| 5,613,072 A | * | 3/1997 | Hammond et al. ............. 705/4 |
| 5,704,044 A | * | 12/1997 | Tarter et al. ................... 705/2 |
| 5,995,939 A | | 11/1999 | Berman et al. |
| 6,324,516 B1 | * | 11/2001 | Shults et al. ................... 705/2 |
| 6,343,310 B1 | * | 1/2002 | DiRienzo .................. 709/200 |
| 2003/0023473 A1 | * | 1/2003 | Guyan et al. .................... 705/9 |

OTHER PUBLICATIONS

StellarNet Releases First Internet -Based Claims Verification Product For Worker' Compensation Industry; PR Newswire; New York: Nov. 1999; pp. 1-3.*
High- tech sleuths by Leslie Werstein Hann. Best's Review. (Property/casualty insurance edition). Oldwick: Nov. 1998. vol. 99, Iss.7; p. 83, 3 pgs).*
Risk & Insurance "Technology: Unlocking the Neural Network" by John Mutch.*
High- tech sleuths by Leslie Werstein Hann. Best's Review. (Property/casualty insurance edition). Oldwick: Nov. 1998. vol. 99, Iss.7; p. 83, 3 pgs.*
Risk & Insurance "Technology: Unlocking the Neural Network" by John Mutch, Jan. 1999.*
Anonymous, "StellarNet Releases First Internet-based Claims Verification Product For Workers' Compensation Industry", Nov. 1999, 3 pages.

* cited by examiner

*Primary Examiner*—F. Zeender
*Assistant Examiner*—Vanel Frenel
(74) *Attorney, Agent, or Firm*—Howard IP Law Group, PC

(57) ABSTRACT

A Workers' Compensation claim verification system uses software accessed at a provider computer. The software checks a centralized Workers' Compensation claim verification system to obtain a Workers' Compensation claim number for use in forms and the like. This eases obtaining of a Workers' Compensation claim number for the provider.

14 Claims, 20 Drawing Sheets

Worker's Compensation Medical Treatment Reporting

First Report (Input Form)

Doctor's First Report of Occupational Injury or Illness

| Patient | History | Findings | Diagnosis | Treatment | Work Status | User Fields |

Patient Information:
LName: ANDERSEN  FName: JIM  SSN#: 494-94-9494  DOI: 10/16/1999

Injury Information:
Report Date: 10/21/1999
12. Injured at: Address: 234 CONTRA COSTA BLD  City: CONCORD  State: CA
    Zipcode: 94549-3003  County: CONTRA COSTA
13. Date and hour of first examination or treatment: 10/16/1999  08:00 ●AM ○PM
14. Date Last Worked: 10/16/1999
15. Date and hour of first examination or treatment: 10/16/1999  09:00 ●AM ○PM
16. Have you (or your office) previously treated patient?  ○Yes ●No
16a. Treated under any health plan for this incident?  ○Yes ●No
16b. Health Plan Name: BLUE CROSS
17. Patient's Description of how the Accident or Exposure Occurred:
 A. Description: "LIFTING A 40# PRODUCE BOX FROM THE FLOOR, WHEN I FELT SHARP BACK PAIN"
 B. Relevant Past History: RECURRENT LUMBAR SACRAL STRAINS
 C. Description of present occupational duties: Heavy Lifting
 D. Relevant leisure activities: WEEKEND FOOTBALL, SKIING, SAILING
 E. Does employee have 2nd job?  ●Yes ○No
 If yes, Employer Name: MT ROSE SKI RESORT

[ Save ] [ Ok ] [ Validate ] [ View ] [ Print ] [ Ok to Send ] [ Suspend ] [ Delete ] [ Cancel ]

for Workers' Compensation

Date and Time: 10/21/99 10:11:01 AM

Doctor's First Report

FIG. 6

Report Page 1  *FIG. 7A*

| DOCTOR'S FIRST REPORT OF OCCUPATIONAL INJURY OR ILLNESS |||
|---|---|---|
| STATE OF CALIFORNIA<br>Form 83012L©1999 | File Copy<br>FROM FIRST CASE | Page 1 of 2<br>Form ID: INS000001000000000Q |

1. INSURER NAME AND ADDRESS  1b. Claim #  REPORT DATE
   ZENITH, 123 COAST DR., SAN FRANCISCO, CA 945-493393  1b. Claim #  10/17/1999
   Telephone Number: 415-339-3939  Fax Number: 415-339-3939

2. EMPLOYER NAME  3. Address No. and Street  City  State  Zip  Telephone #
   LUCKY STORES  234 MARINA WAY  SAN LEANDRO  CA  945-493393  510-499-4949
4. Nature of Business: GROCERY STORE  Policy Number: 499-49-499-4  Fax Number: 510-393-9393

5. PATIENT NAME (first name, M.I., last name)  6. SEX  7. Date of Birth  Mo  Day  Year
   JIM ANDERSON  234 MARINA WAY  ☑ Male  ☐ Female  10  14  1949

8. Address  City  State  Zip  9. Home Tel #  Work Tel #
   1744 RELIEZ VALLEY RD.  LAFAYETTE  CA  945-498888  925-838-3838  925-884-8484

10. Occupation (Specific Job Title)  11a. Social Security #  11a. Date of Hire  11c. Patient Account #
    JOURNEYMAN CLERK  494-94-9494  10/25/1994  9-49-49-49-49-4

12. Injured At  City  State  Zip  County
    123 CONTRA COSTA RD.  CONCORD  CA  945-493003  CONTRA COSTA 13. Date and hour of injury  Mo  Day  Year  Hour  14. Date Last Worked:  Mo  Day  Year
    or onset of illness:  10  17  1999  08:00 AM  10  16  1999

15. Date and hour of first  Mo  Day  Year  Hour  16. Have you (or your office) Previously
    examination or treatment:  10  17  1999  09:00 AM  Treated Patient?  ☑ Yes  ☐ No 16a. Treated under any Health Plan for this Incident?  ☑ Yes  ☐ No  16b. Health Plan Name?:  BLUE CROSS 17. PATIENT'S DESCRIPTION OF HOW THE ACCIDENT OR EXPOSURE OCCURRED:
    A. Description: "LIFTING A 40LB PRODUCT UP FROM THE FLOOR, WHEN I FELT SHARP BACK PAIN."
    B. Relevant Past History: RECURRENT LUMBARSACRAL STRAINS
    C. Description of Previous Occupational Duties: Heavy Lifting
    D. Relevant Leisure Activities: WEEKEND FOOTBALL, SKIING, SAILING
    E. Does Employee have 2nd job?  ☑ Yes  ☐ No  If Yes, Employer Name: MT ROSS SKI RESORT 18. SUBJECTIVE COMPLAINTS:
    A. Description: ""SHARP LOW BACK PAIN"
    B. Symptoms:

| Body Part | Onset | Quality | Frequency | Severity | Precipitating Activities |
|---|---|---|---|---|---|
| Lower Back | Sudden | Sharp | Constant | Moderate | Lifting, Bending, Sitting |

19. OBJECTIVE FINDINGS:
    A. Vital Signs:
       BP: 120/80  HT: 5'8"  WT: 190  Pulse: 78  Temp: 98.6  Resp: 18 /min
       Allergic to any medications?  ☐ Yes  ☑ No  If Yes, specify:
    B. Focused Physical Exam:
       45 DEGREES LUMBAR FLEXION WITH POSITIVE RIGHT STRAIGHT LEG RAISE AT 60 DEGREES
    C. X-Ray and Laboratory Results:
       NONE
    D. Job Description Reviewed:  ☐ Yes  ☑ No 20. DIAGNOSIS: (if occupational illness, specify _____ agent used _____ of _____ )
    A. Description  B. ICD9 Codes
    SPRAIN LUMBAR SACRAL  8460
    C. Chemical Or Toxic Compounds Involved?
    If yes, explain:
    D. Other Relevant Diagnosis Report Page 2

*FIG. 7B*

Page 2 of 2

... CONTINUED DOCTOR'S FIRST REPORT OF INJURY... ANDERSON, JIM 9-49-49-49-49-4

21. ARE FINDINGS AND DIAGNOSIS CONSISTENT WITH PATIENT'S ACCOUNT OF INJURY
OR ONSET OF ILLNESS?   ☑ Yes  ☐ No
If no, explain:
A. Did work cause or contribute to the injury or illness? ☑ Yes  ☐ No  ☐ Cannot Determine
If no or cannot determine, explain:
B. Is the patient permanent and stationary?         ☐ Yes  ☑ No    If yes, Date:
C. If no, _____ permanent and stationary date:    11/05/1999
D. Is permanant disability anticipated?              ☐ Yes  ☑ No 22. IS THERE ANY OTHER CURRENT CONDITION THAT WILL DELAY PATIENT'S RECOVERY?  ☑ Yes  ☐ No
If yes, explain: Pain surging to other body parts.

23. TREATMENT RENDERED:
A. First Aid          ☐ Yes  ☑ No
B. Treatment Date     Treatment                    C. Procedure Codes
   10/17/1999         OFFICE/OUTPATIENT VISIT, EST    99212
D. Instructions to Patient:  ERGONOMIC EDUCATION, HEAT AND LOW BACK EXERCISES.
E. Referrals:
F. Disability status: Discharged as _____ with no need for further medical care?  ☐ Yes  ☑ No
G. If discharged, Discharge Date:

24. IS FURTHER TREATMENT REQUIRED?    ☑ Yes  ☐ No
A. Medication: VICODIN              B. Physical Therepy:  2  per week for 3   weeks
C. If Surgery, type:                                  CPT Codes
D. Diagnostic Tests:
E. Estimated Duration of Treatment:   25 days      F. Return Visit Interval: ONE WEEK
G. Recommended Referrals:
H. Treatment Plans, Other:

25. IF HOSPITALIZED AS INPATIENT, Give Hospital Name and Location: Date Adm: Mo Day Yr.  Est. Stay: Days 26. WORK STATUS:
A. Is Patient able to Perform Usual Work?  ☐ Yes  ☑ No
B. If not, date when Patient can return to Regular Work:    10/30/1999
C. If not, date when Patient can return to Modified/Transitional Work:   10/30/1999
D. Restrictions: Specific functional limitations/frequency and weight restrictions
   based on an 8 hour work day.
   Key: (U)nable, (S)eldom=<1%, (O)ccasional=1-33%, (F)requent=34-66%, (C)ontinuous=67-100%
   Ability              Limitation            Weight Limit
   Repetitive _____     Seldom=<1%
   Lifting from Floor   Unable
   Lifting from Waist   Occasional 1-33%      MAX 15lbs
E. Restrictions Narrative:
F. Is employee likely to become a Qualified Injured Worker?  ☐ Yes  ☑ No 27. Doctor's  Name and Degree:   CLIFF L. WILSON, MD                 IRS#: 3939334481
              Facility Name:  FIRST CARE                    CA License #: CA2338193483
                 Address:  123 TAYLOR ST, LAFAYETTE, CA 945468880   Specialty: OCC MED
              FPO Networks:                              Doctor's Telephone #: 925-384-8505
           <<< DOCTOR'S SIGNATURE ON FILE AT DOCTOR'S OFFICE >>>
Any person who makes or causes to be made any knowingly false or fraudulent material statement or material representation for the purpose of obtaining or denying worker's compensation benefits or payments is guilty of a felony.

Input Form e-StellarNet

Claims Verification Service - Microsoft Internet Explorer

Claims Verification Service

Enter Patient detail( *All fields are required.* )
Click *here* for batch verification.

| Last Name: | SMITH | First Name: | Sue |
| SSN: | 565340665 | Date of Injury: | 10-24-1999 |
| Employer: | Railway Express | Payer Name: | CSSG |

[Submit] [Reset]

Back  Home  Demo Menu

*FIG. 8A*

Result Page

Claims Verification Service - Microsoft Internet Explorer e-StellarNet

Claims Verification Service

Patient details

| | | | |
|---|---|---|---|
| Last Name: | SMITH | First Name: | Sue |
| SSN: | 565340665 | Date of Injury: | 10/24/99 |
| Employer: | Railway Express | Claim Number: | CA334848399 |
| Payer Name: | CSSG | Payer ID: | WC034 |

Click *here* to perform another lookup.

Back  Home  Demo Menu

Inquiry Email (Form)

e-StellarNet

Provider Payment Status Inquiry Email

An email will be sent to SUNNY@CSWL.COM in the following format

Medical Payment Status

Date: 12/6/99
         From: Sunny Paul (sunny@cswl.com)
RE: Employee Name: BOBO NEIL
    Employer Name: MARINE WORLD
       Claim No. 6100610299961195
          SSN: 389705260
    Date of Injury: 7/22/95
Please advise status on the following invoice:
  Date of Service: 10/1/99
  Account/Invoice no: 7A9832
    Provider Name: DR. KEN ANDERSON
     Provider TIN: CAI798321
   Date of Invoice: 10/1/99
All Control Number: CMMC10932
      Comments: Thank you for your help

[Send It] [Cancel]

Back    Home    Demo Menu

Received Email

```
Provider Payment Status Inquiry                                    _ □ X
File  Edit  View  Tools  Compose  Help
🖬 🖶 ✕ 🖴 🔍 🖼 ⇦ ⇨ 📄 🗂 🗑 ✉ 📧
```

From: Sunny Paul
Date: Monday, December 06, 1999 8:14 PM
To: SUNNY@CSWL.COM
Cc: sunny@cswl.com
Subject: Provider Payment Status Inquiry

MEDICAL PAYMENT STATUS

Date : 12/6/99
From: Sunny Paul (sunny@cswl.com)
Re: Employee Name : BOBO NEIL
    Employer Name : MARINE WORLD
    Claim No : 610061029996195
    SSN : 389705260
    Date of Injury : 7/22/95

Please advise status on the following invoice :

Date of Service : 10/1/99
Date of Invoice : 10/1/99
Account/Invoice mo: 7A9832
Provider Name : Dr. KEN ANDERSON
Provider TIN : CA1798321
BILL CONTROL NUMBER : CMMC10932
Comments :
Thank you for your help
Click
http://www.e-stellernet.com/application/inqemail/response.asp?rdn=112
to reply to this mail

Response Form e-StellarNet

Provider Payment Status Inquiry – Response Email Form

To Medical Facility : sunny@cswl.com

Bill Control No: (BCN): CMMC10932 (For future reference please use the above BCN)

The status of above invoice is:

- ● Our records indicate payment was released on [10/28/1999]
- ○ Our records indicate payment was paid in accordance with our contract agreement.
- ○ No further payments are recommended
- ○ Claim is currently under review for medical necessity
- ○ Claim is currently under AOE/COE investigation.
- ○ Claim was denied
- ○ Necessity for this service is currently under review.
- ○ No Policyholder Under This Name.
- ○ We do not have coverage for this employer for this Date of Injury.
- ○ No Industrial Injury Reported By Employer.
- ○ Doctor's First Report Needed.
- ○ Current Medical Report Needed
- ○ Itemized Statement Needed.
- ○ Other [    ]

[Next Page] [Reset]

Back Home Demo Menu

StellarNet On-Line Bill Submission Form e-StellarNet On-Line Bill Submission

Welcome to StellarNet's on-line bill submission page. Please complete the form:

1. If you are not registered, click here to go to registration page.

2. Registered members, proceed with bill submission:

a. Input your email address in the first box and click on "Report" to double check your membership status. If you are not registered, or if the email address is incorrect, you will get an error message.

b. To submit your bills use the "Browse..." button to select the name and location of the file(s) to submit. You can submit up to 3 files at one time.

c. To submit the bills, click "Upload file(s)" to submit bills.

If you are a first time submitter, you will receive an acknowledgement back within 48 hours after you have submitted your first batch of bills. Thereafter, you will receive the acknowledgement back within 24 hours of submitting your bills.

Please press the TAB key NOT the ENTER key to move down. Use Shift TAB to move up.

Member Upload Password or Email: [_____] [Report]

Files To Upload:
 File 1: [_____] [Browse]
 File 2: [_____] [Browse]
 File 3: [_____] [Browse]
 [Upload File(s)]  [Reset Form]

Use browser's BACK button to return to previous page.

If you have eany questions...

Call us at 415/882-5700, or Email us at rtwfast@ibm.net

*FIG. 10B*

| Field Name | Len | Type | Description / Example |
|---|---|---|---|
| Payer ID | 9 | Char | Electronic payer ID example: WACA02012. Print and mail payer ID is always PM0000000. |
| Patient's SSN | 9 | Char | Example: 123680000 |
| Date of Injury | 8 | Char | MMDDYYYY Jan 20, 2000 example: 01202000 |
| Date of Service | 8 | Char | MMDDYYYY Jan 21, 2000 example: 01212000 |
| Type of Service | 1 | Char | 1=Medical Care, 2=Surgery, 3=Consultation, 4=Diagnostic X-ray, 5=Diagnostic Laboratory, 6=Radiation Therapy, 7=Anesthesia, 8=Assistance at Surgery, 9=Other Medical Service, 0=Blood or Packed Red Cells, A=Used DME, F=Ambulatory Surgical Center, H=Hospice, L=Rental Supplies in the Home, M=Alternative Payment for Maintenance Dialysis, N=Kidney Donor, V=Pneumococcal Vaccine, Y= Second Opinion on Elective Surgery, Z=Third Opinion on Elective Surgery. |
| Provider Tax ID + Sub ID | 13 | Char | 1234567890000 (use 0000 if not using Sub ID) |
| Submit Date and Time | 12 | Char | MMDDCCYYHHMMSS Jan 22, 2000 9:30 01 am example: 01222000093001 |
| Payer Name | 25 | Char | ABC WC PAYER |
| Payer Address | 25 | Char | 100 MAIN STREET |
| Payer City State Zip | 25 | Char | BIG CITY, NY 00030 |
| Claim Number | 28 | Char | 20303200223 |
| Type of Document | 2 | Char | 01=First Report, 02=Supplemental Report, 03=P&S Report, 04=QME, 05=Consult, 06=AME, 07=Entire File, 08=Diagnostic, 09=Chart Notes, 10=Pre-Authorization Request, 11=Referral Request, 12=Disability Status, 13=Surgical, 14=Ambulance, 15=Ancillary, 16=Home Care, 17=Other |
| ICD9 | 6 | Char | Primary Diagnosis Code, no spaces no period on 5 digit codes. |
| Period | 1 | Char | (also known as dot) |
| File Type | 3 | Char | Original file extension, DOC, RTF, TXT, etc. |

*FIG. 12*

On-Line WS Reports and Attachments Submission

Welcome to e-StellarNet's on-line report submission page. Please fill out this form completely for quick delivery to the proper administrator. <u>Demonstration</u>
If you are not registered: <u>click here to register.</u>

Please press the TAB key NOT the ENTER key to move down. Use Shift TAB to move up.

Member Upload Password or Email: [_____] [Reset]

Local Local Zip File of All Attachment Files or
Single Attachment File to Upload [_____] [Browse...]

[Upload Zip File]

Only fill out these following fields if
sending a single, non-zipped, attachment file.

Payer ID: [_____]
Patient Social Security No: [_____]
Date of Injury: [_____]
Date of Service: [_____]
Provider Tax ID: [_____]
Type of Service Code: [Medical Care ▾]
Your Initials and ID: [_____]

[Upload Report File]

Use browser's BACK button to return to previous page.

*FIG. 13*

WORKERS COMPENSATION INFORMATION PROCESSING SYSTEM

BACKGROUND OF THE INVENTION

The present invention relates to Workers' Compensation information processing systems.

Workers' compensation is a class of insurance mandated by States and the federal government whereby employers provide employees with medical and disability benefits for injuries or illness incurred in the course and scope of their employment. Unlike other classes of insurance, workers' compensation insurance does not require written documentation that identifies individual covered employees.

Workers' compensation insurance obtained from an insurer, or which is financed by the employer (self-insurance), is based upon underwriting criteria that includes payroll, number of employees, job classifications, aggregated loss experience (non-personal) and actuarial modifiers. Insurers and self-insurers—payers—typically do not maintain lists of covered employees.

For this reason, when an employee incurs an injury or illness and seeks treatment, matching the claim to the payer responsible for payment is difficult. Typically neither the injured employee nor the medical provider knows or has access to the workers' compensation claim identifier the payer requires to make a payment for medical services rendered. Identity of the payer typically also is not known. This leads to delays in claim administration, poor coordination of treatment between the payer and the provider (often to the detriment of the injured employee) and untimely payment for medical services rendered.

When the work-related injury or illness occurs, the employer must report the occurrence to the payer (insurer, self-insurer, or third-party administrator), who then creates a claim file with a specific claim number. All subsequent communications and transactions depend on, are routed and administered according to this claim number. The claim number is essential to efficient operation of a workers' compensation system. The claim number is the payer's key identifier for file management, work flow routing, document matching, data capture and payment transactions. In order to receive prompt payment, a medical provider must provide the claim number when submitting bills and reports. It is often the case that the provider has no knowledge of or access to the claim number.

Providers such as physicians and pharmacists will often send bills without the claim number because a claim number has not been assigned, or because of the administrative difficulties of obtaining the claim number. Bills without the claim numbers produce a substantial burden of unmatched mail for the payer.

One Workers' Compensation industry survey has indicated that as many as fifty percent of provider bills, reports and attachments are received by the payer without claim numbers. Fifty percent of this number, or twenty-five percent of the total, typically do not match any injury within the payer's claim system. Bills lacking claim numbers cause a great deal of difficulty for the payer's bill-verification systems, rendering them slow, duplicative, prone to error, and costly to administer.

In the current typical Workers' Compensation payment system, the process of producing claim numbers is often protracted. For example, the employer may not report the Workers' Compensation claim for a relatively long period of time and thus no claim number is set up, even though the injured worker has sought and received medical treatment. Thus, when the injured party goes to the provider, the provider is unable to find a claim number and has no choice but to produce a bill without the required claim number. This bill can take some time working its way through the payer's system. Later the employer is prompted by the payer to report the claim.

In addition, when the payer's recognition of medical treatment of an injured worker is delayed because a claim number has not been matched to the medical bill or report, the report of injury by the employer, prompted by the payer, is typically delayed. Slow reporting by the employer delays medical management by the payer and increases the cost of the claim. For example, in one study by a major Workers' Compensation insurer, the costs of a claim decreased three percent for each day that reporting was shortened between 21 to 7 days. Another large Workers' Compensation insurer found that claims reported within 10 days were 47% less costly than those reported in 31 days.

It is desired to produce an improved Workers' Compensation information processing system.

SUMMARY OF THE PRESENT INVENTION

One embodiment of the present invention is a Workers' Compensation claims verification system (workers' compensation claim number indexing system) which includes software accessed at a provider computer. The software accessed at the provider computer is adapted to allow the provider to input data concerning a Workers' Compensation claim, the software being adapted to send an electronic claim number request containing identifying data to a Workers' Compensation claims verification system. The Workers' Compensation claims verification system is constructed to receive the data and determine therefrom any matching Workers' Compensation claim number. If there is a matching Workers' Compensation claim number, the Workers' Compensation claims verification system is adapted to electronically supply the matching Workers' Compensation claim number to the provider computer. If there is no matching Workers' Compensation claim number, the Workers' Compensation claims verification system is adapted to electronically report to the payer that a claim exists without a claim number.

Another embodiment of the present invention concerns a Workers' Compensation medical treatment reporting system including software accessed at a provider computer and electronic report-filtering software accessed at a payer computer. The software accessed at the provider computer is adapted to prompt the provider to input data concerning a Workers' Compensation claim. The software is adapted to send a Workers' Compensation medical treatment report electronically to a payer's computer. The electronic report-filtering software at the payer computer is adapted to direct the electronic report as a result of predetermined criteria. The electronic Workers' Compensation medical treatment reports that meet a human review criteria are sent directly to a case manager for review. Other electronic Workers' Compensation medical treatment reports are automatically directed to be processed.

BRIEF DESCRIPTION OF THE DRAWINGS

FIG. 6 is a diagram illustrating an electronic input form for a doctor's first report of an occupational injury or illness.

FIGS. 7A and 7B show a formatted output of the doctor's first report of occupational injury or illness.

FIG. 8A shows an input form for the claim verification service of one embodiment of the present invention.

FIG. 8B illustrates a response to the provider of the claim verification service of the Workers' Compensation system of one embodiment of the present invention.

FIG. 9A is an inquiry E-mail form which can be input by the provider and sent through a Workers' Compensation server to a payer to check on the status of a Workers' Compensation bill.

FIG. 9B is an E-mail of the Workers' Compensation status check sent to payer.

FIG. 9C is a form which is accessed by the payer to give a response to a provider payment status inquiry in one embodiment of the present invention.

FIGS. 10A and 10B illustrate examples of web site pages from a Workers' Compensation system server in one embodiment of the present invention.

FIG. 12 is a chart that illustrates one example of a renaming protocol of one embodiment of the present invention.

FIG. 13 is a illustration of a web page which can be used with one embodiment of the attachment system of the present invention.

DETAILED DESCRIPTION OF THE PREFERRED EMBODIMENT

One embodiment of the present invention provides an end-to-end Internet connectivity solution for the workers' compensation industry which eliminates phone, fax and mail transactions involved in medical treatment reporting, claims for payment, and payment for the services rendered.

This business system is made up of a number of discrete components or sub-systems. These components or sub-systems are described below.

1. Claims Verification (Claims Indexing, Automated Indexing or Auto-Indexing): A system where a provider can electronically submit an injury description against a database of claim information and obtain a claim number. This system eliminates the current time-consuming manual process.

2. Early Notice of Loss: When an inquiry against the claims verification file results in "no claim found," the system automatically sends a notice to the payer advising the payer than an injury is being treated. This notice allows the payer to take appropriate action.

3. Attachment Processing: Many bills require an accompanying report known as an attachment. Attachments are not standard forms. One embodiment of the system of the present invention allows the downloading of any type of form, which is given a unique identifier, to be transmitted to receiving software. This software then matches the bill and the attachment for further processing.

4. Report Triage System: The business system provides software which resides at a user's site. This system directs incoming formatted reports and selects which reports are to be automatically routed to a case manager.

5. Payment Status Inquiry: This payment status inquiry replaces phone, fax and mail inquiries as to the present status of a workers' compensation bill.

6. Electronic Remittance Advice: Presently, for every bill which is submitted by a provider and paid by the payer, a paper document is sent with the payment to the provider. The business system processes these different transactions and electronically converts them into a standard format, sorts by payer, aggregates and delivers to the payee (provider) where they can be automatically uploaded to post cash.

7. Electronic Report of Treatment and Treatment Plan: This part of the business system automates the completion and submission of injury treatment reports. It contains a number of automated aids, as set forth in the description with the physician's full worksheets.

8. Electronic Bill Submission: This is a part of the overall business process.

9. Electronic Fund Transfer System: Once the bill has been processed and authorization is obtained from both sides, the bills can be paid automatically with an electronic transfer between provider and payee.

Figure 1:
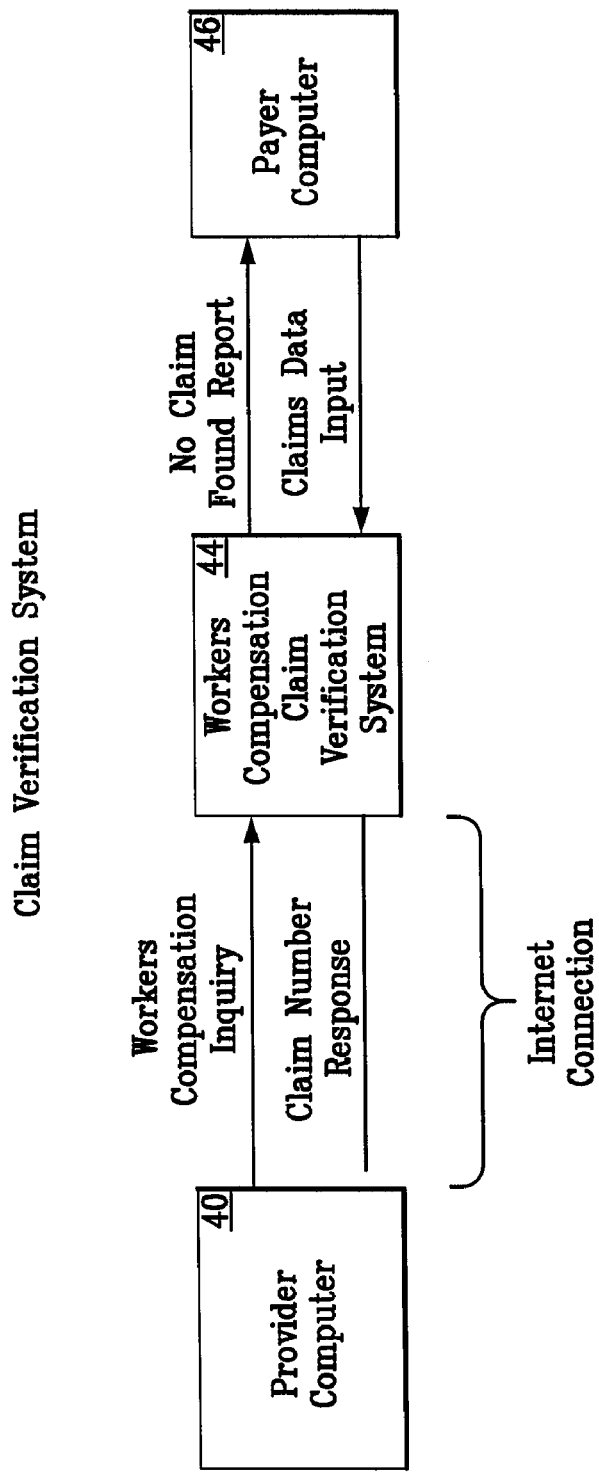
FIG. 1 is a diagram of a Workers' claim-verification system of one embodiment of the present invention.

FIG. 1 illustrates a Workers' Compensation claim verification system of one embodiment of the present invention. A provider computer 40 has access to Workers' Compensation software which can be stored at the server or at the provider computer. The provider can be a doctor, pharmacy or other medical professional. The provider computer is operably connected with the Workers' Compensation claim verification system 44. In a preferred embodiment, this connection is an Internet connection. Typically, multiple provider computers have such a connection to a single Workers' Compensation claim verification system 44. Registered providers are provided with access to the Workers' Compensation claim verification software. The Workers' Compensation software prompts the provider to input data sufficient to identify a Workers' Compensation claim. This data includes name, social security number, and injury date. The injury date is used to distinguish a particular injury claim for workers with more than one injury claim. Additional data such as employer number and insurer name can also be provided. The user provides the necessary data to the Workers' Compensation claim verification system 44.

In a preferred embodiment, a number of different providers (not shown) are connected to the Workers' Compensation claim verification system 44. The Workers' Compensation claim verification system 44 searches an associated database by querying it with the relevant data provided from the provider computer. If a matching Workers' Compensation claim number is found, a claim number response is sent from the Workers' Compensation claim verification system back across the Internet to the provider computer 40. In one embodiment, the Workers' Compensation software from the payer computer uses the claim number in the production of bills and medical treatment reports. If no matching Workers' Compensation claim number is found in the database, the Workers' Compensation claim verification system produces an indication to that effect. In a preferred embodiment, this indication is an early e-mail alert that is sent to the payer computer 46. Once a claim number is determined, this claim number can be sent from the payer computer 46 to the system 44. Otherwise, the system 44 can be updated during the normal database update process.

Data for a number of payer computer systems is stored in the database for the Workers' Compensation claim verification system. The data for the database is preferably obtained from the payer. Bill review systems typically have contracts with a number of different payers to review the bills, and thus would have information which would allow a match of a Workers' Compensation claim number with other relevant data. A payer computer 46 produces this data, and sends it to the bill review system's computers. The bill review system's computers can then provide the data to the Workers' Compensation claim verification system which allows for interaction with the provider computers. Optionally, the data can be supplied directly from the payer's computer.

The Workers' Compensation claim verification system has a number of advantages. It allows for quick claim number response for the provider. The Workers' Compensation claim number can be obtained easily. This increases the provider's likelihood of attempting to get a Workers' Compensation claim number.

Additionally, In one embodiment, the Workers' Compensation software includes medical report and billing software which automatically makes inquiry as to the Workers' Compensation claim number and inserts the claim number, once obtained, into reports and bills to be sent out. The system automatically attempts to get a Workers' Compensation claim number whenever a report or bill is to be transmitted.

The advantage of the system of the present invention for the payer is that more of the reports and bills are received having a Workers' Compensation claim number attached. This reduces the number of unmatched bills and speeds up the processing of the reports and bills. The correct bills can be paid quickly which reduces the problem of duplicate bills.

The Workers' Compensation claim verification system 44 is also not payer system dependent. Multiple payers' data can be stored in the Workers' Compensation claim verification system 44. The provider need only interface with the Workers' Compensation claim verification system 44 rather than interfacing with a variety of different payers.

The system of the present invention speeds up the payment of bills to the provider, thus providing an advantage to the provider. The payer computer systems are more likely to be notified of a Workers' Compensation claim which requires a Workers' Compensation claim number. This prompts the employer to more quickly report the incidents and for the providers to more quickly report their treatments. The total system costs for each claim can be reduced since the delay in the system is reduced.

Note that the Workers' Compensation inquiry sent to the Workers' Compensation claim verification system can be batched in some circumstances. For example, for large-scale providers such as billing services, it makes sense to batch all inquiries until nighttime.

The Workers' Compensation claim verification system of the present invention can be arranged in alternate ways. If a large number of provider computers and payer computers become associated with the Workers' Compensation claim verification system, the system in effect acts as a clearing house for a large amount of Workers' Compensation claim number data.

In another embodiment of the present invention, the payer's computer sends to the Workers' Compensation claim verification system computers a block of unused Workers' Compensation claim numbers. The Workers' Compensation claim verification system then provides an unused claim numbers to the provider computer upon receiving a request. The verification system then sends an indication of the distributed Workers' Compensation claim number and other data concerning the claim to the payer computer. This embodiment has the advantage that a claim number is sent to the provider as soon as possible. The downside of this embodiment is that it requires the Workers' Compensation claim verification system to carefully monitor the block of unused claim numbers to avoid fraud.

Another embodiment of the present invention is a system in which the Workers' Compensation claim verification system server contains software which allows the provider computer and the payer computer to directly interface with one another. The provider computer and the payer computer obtains the software from the server as needed. The software preferably allows the provider computer to directly interface with the payer computer across the Internet. The downside of this system is that software updates need to be distributed to all the provider and payer computers, which can be difficult and can cause compatibility problems and makes it harder to do software upgrades.

Figure 2:
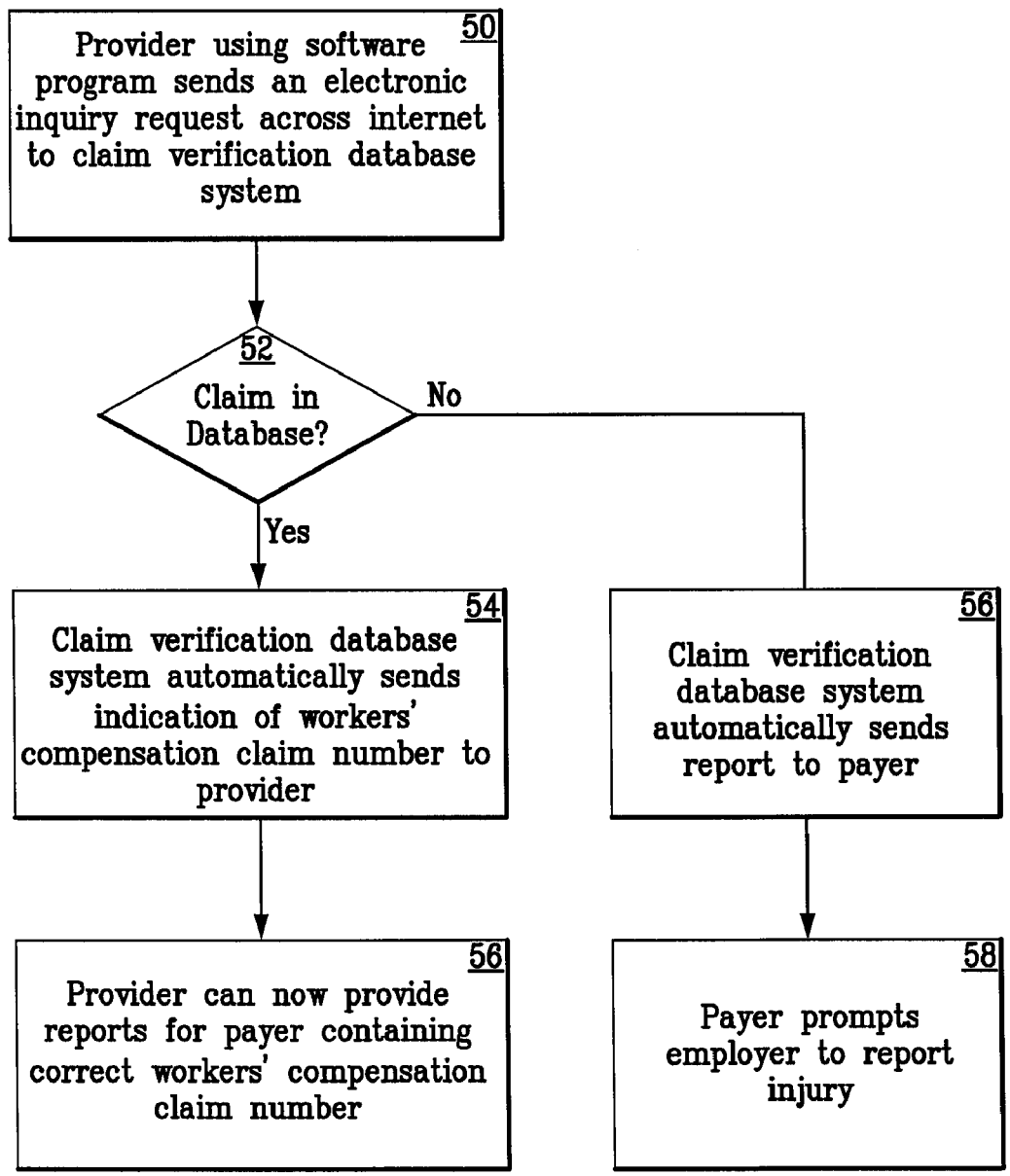
FIG. 2 is a flow chart that illustrates the operation of the Workers' claim-verification system of FIG. 1.

In one embodiment of the present invention, the Workers' Compensation claim verification system software can be directly loaded into a payer's computer. The provider can access the Workers' Compensation claim verification system software at the payer computer and this software allows the obtaining of a claim number by the provider directly from the payer computer. In that case, if no claim number is found, an indication is produced which causes the payer computer to produce a message, to the payer distributing the Workers' Compensation claim numbers or sends an electronic message to the software which produces the Workers' Compensation claim numbers. This system also has the downside that it requires frequent software updates to distributed locations. For these reasons, the preferred embodiment of the present invention is one in which a centralized Workers' Compensation claim verification server is used to give the Workers' Compensation numbers to a provider computer as well as produce early updates of a lack of a claim number on a claim to the payer computer FIG. 2 is a flow chart that illustrates the operation of the system of FIG. 1. In step 50, the provider, using the software program, sends an electronic inquiry request across the Internet to the Workers' Compensation claim verification system. In step 52 it is determined whether the inquiry refers to a claim number in the Workers' Compensation claim verification system's database. If so, in step 54, the claim verification system automatically sends an indication of the Workers' Compensation claim number to the provider. In step 56, the provider produces reports for the payer containing the correct Workers' Compensation claim number. In step 56, if the database does not contain the claim number, the claim verification system automatically sends an early alert message to the payer. In step 58, the payer prompts an employer to provide a claim incident report, submission of which allows a payer to assign a Workers' Compensation claim number.

Figure 3:
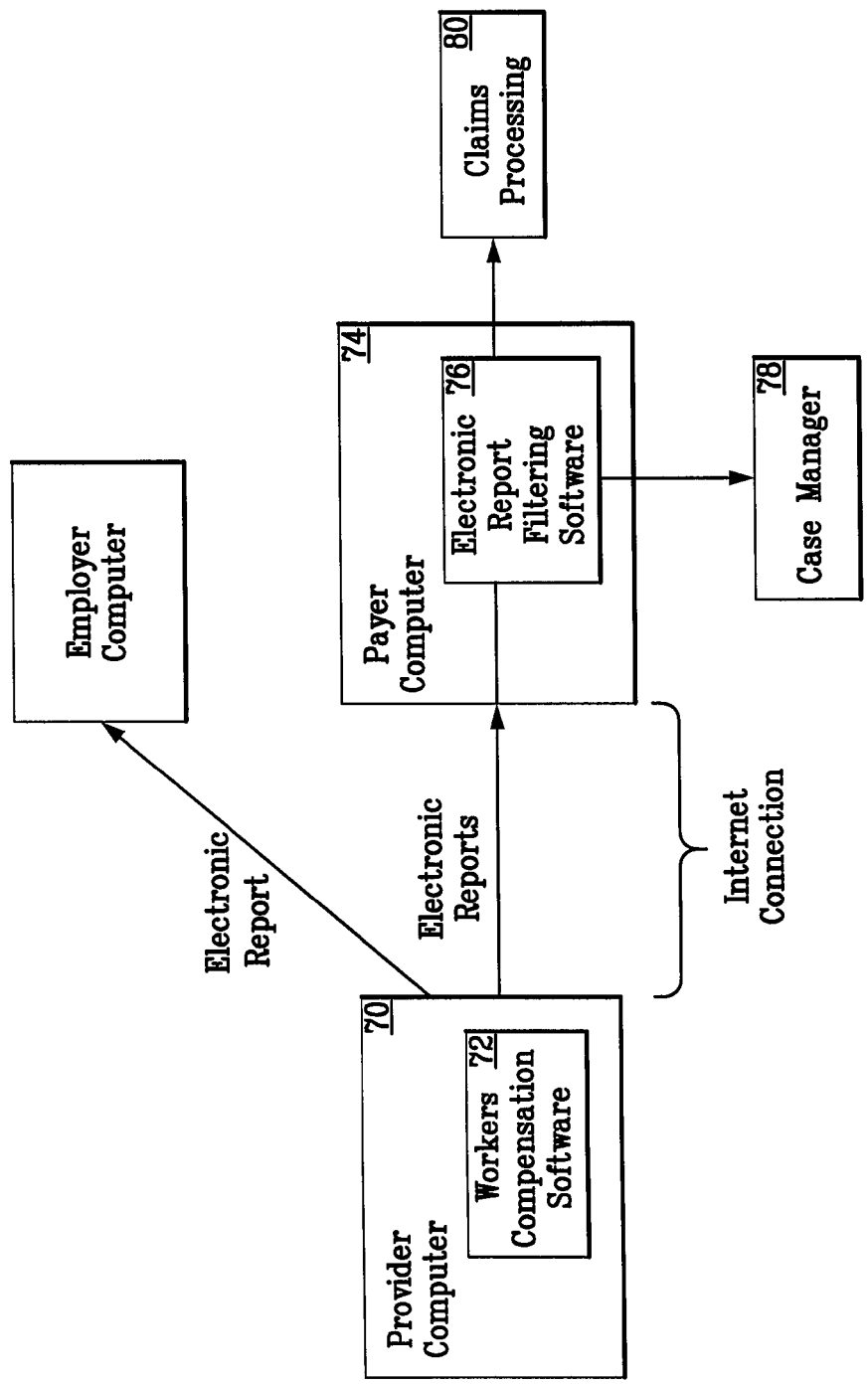
FIG. 3 is a diagram of a Workers' Compensation medical treatment reporting system of one embodiment of the present invention.

FIG. 3 is a diagram that illustrates a Workers' Compensation medical treatment reporting system of one embodiment of the present invention. The provider computer 70, including the Workers' Compensation software 72, which can be downloaded from the server, produces electronic reports which are sent to the payer computer 74. In a preferred embodiment, these electronic reports are sent over the Internet. The Workers' Compensation software 72 prompts the user to input the required data for the medical treatment reports. Many states have different requirements, and the Workers' Compensation software can either request a superset of all the data required in each state or a request based upon the applicable state's laws. The data for the medical treatment reports can be automatically adjusted into the format required by each state's laws. The electronic reports preferably are given the Workers' Compensation claim number by the operation of the Workers' Compensation claim verification system of FIG. 1.

The payer computer 74 preferably contains an electronic report filtering software 76. This electronic report filtering software 76 examines the electronic reports automatically, based upon predetermined criteria, to determine whether a given medical treatment report should be sent to a human case manager or whether the bill should be automatically processed. The criteria used by the electronic report filtering system 76 is set based upon data input by the payers. In one embodiment, default criteria are used which can then be modified by the payers. For example, certain treatments, such as head-injury cases, would typically be flagged as requiring review by a human case manager 78. On the other hand, sprains and other such minor injuries would typically be flagged to be automatically processed without case manager review. Other criteria used can be based upon fraud statistics, the provider involved, and the seriousness of the cases. The electronic report filter software uses the predetermined criteria to examine the medical treatment electronic reports for distribution. This can be done using Boolean logic formulas based upon the medical treatment report form inputs, where the electronic report filtering software will search, based upon the predetermined criteria, for reports to be sent to the case manager 78. This electronic report filtering software 76 provides the case manager with only the more relevant cases. This is an advantage because the case manager need not review the majority of reports which do not need human review. In one estimation, about 15% of the treatment reports should be reviewed by a case manager. A much greater number—the remaining 85% of the reports—should be automatically sent for processing. The medical treatment reporting system of the present invention can substantially reduce the number of medical treatment reports that need to be reviewed by a case manager.

Figure 4:
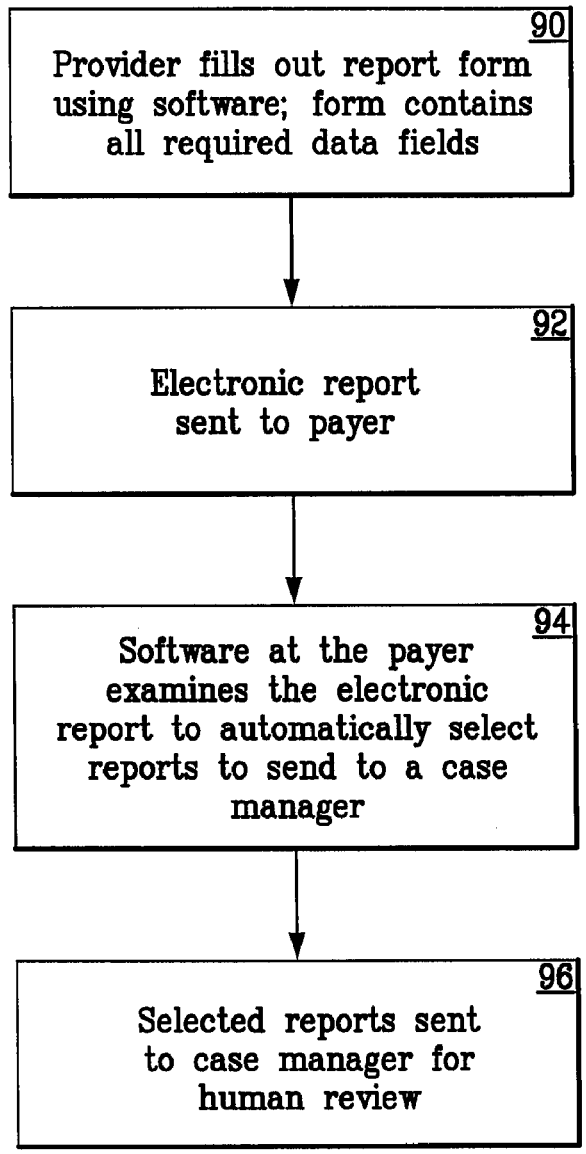
FIG. 4 is a flow chart that illustrates the operation of the Workers' Compensation medical treatment reporting system of FIG. 3.

FIG. 4 is a flow chart that illustrates the operation of the system of FIG. 3. In step 90, the provider fills out a report form using software. The form contains all the required data fields. In step 92, the electronic report is sent to the payer. In step 94, the software at the payer examines the electronic report to automatically select reports to send to a human case manager. In step 96, the sorted reports are sent to the case manager for human review. Other reports are automatically sent to a payment department for payment.

Figure 11:
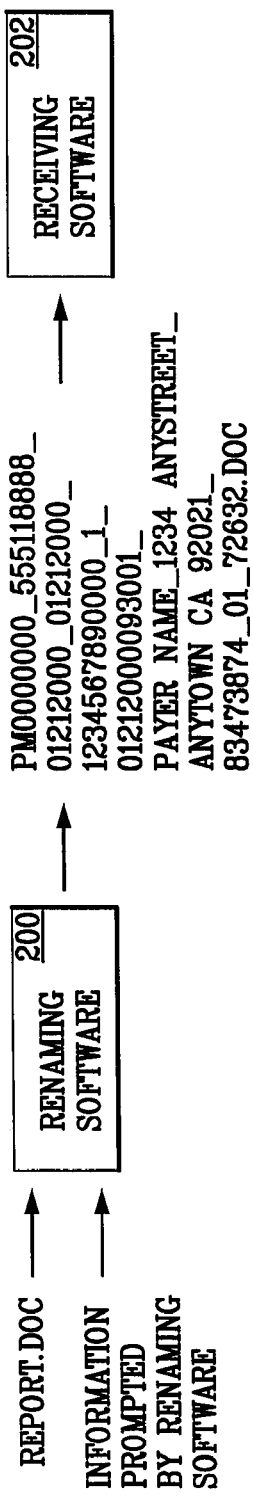
FIG. 11 is a diagram that illustrates an attachment system of the present invention.

FIG. 11 is a diagram that illustrates an attachment system of the present invention. Prior systems that electronically send attachment files have the disadvantage that it can be difficult to match the attachments with the bill. For example, consider the case of an X-Ray or magnetic resonance imaging (MRI) attachment files that are stored in a proprietary file format. A system routing the attachment files may not be able to open the file in the correct manner. This can result in unmatched attachment files that require a significant amount of manual work to connect together.

One embodiment of the present invention is an attachment system that uses renaming software to rename the file title using information fields. The file title then contains information that can be used by a receiving software system to route and handle the attachment file.

Looking at FIG. 11, the renaming software 200 receives the file, in this case named "Report.doc." The renaming software 200 prompts the user to input data which is used in the renaming of the file. The data preferably contains information that allows the receiving software 202 to automatically route the attachment to the correct place and maintain the attachment of the file to another electronic file such as an electronic bill. In the example of FIG. 11, the renaming software produces a renamed file title using input data. The file title includes a number of different fields which contain important information to allow the attachment of the attachment file to a main file such as an electronic bill. Other data, such as data from the bill or other reports, accessible by the renaming software, can also be put into some of the data fields of the file name.

FIG. 12 illustrates an example of an attachment name protocol which is implemented by the renaming software. The file extension (.doc, .rtf, .txc, etc.) is not affected by the renaming software. By not changing the file extension, the system allows the software that operates upon the different file types to be unaffected by the renaming. In addition to the file extension, additional data fields are used by the renaming software. The field data can be used to identify the attachment in a uniform manner. The data in the fields is sufficient to identify the attachment file to a bill.

In one embodiment, many of the fields are useful to identify healthcare-type attachments. Attachment that can be used in healthcare can include reports, X-Rays, and the like. In one embodiment of the present invention, the Workers' Compensation claim number field is provided. This allows a Workers' Compensation claim number to be produced in a field of the attachment's name, thus allowing for the easy identification of the claim number to the attachment. Other fields that can be used include a payer ID field, a patient security number field, date of injury field (useful to distinguish multiple Workers' Compensation injuries for a single patient), a date of service field that indicates the date of the medical services provided, a type of service field, a provider ID field, a submit date and time field that acts as a time-stamp which can distinguish between identical copies of an attachment submitted at different times. The payer name, payer address and payer city, state and ZIP fields allow for the mailing of the attachment to the payer if there is no electronic connection made with a given payer. The type-of-document field helps the receiving software route the document in the correct manner. Also, a primary diagnosis code field is provided indicating the primary diagnosis. Not all of these fields need to be used with the present invention. The attachment system of the present invention can be used not only for the Workers' Compensation systems but could also be used for the larger healthcare attachment files or even other types of insurance attachment files. These areas also have the problem of electronic files which need to be associated with a main file such as an electronic bill.

In a preferred embodiment, the different fields are separated by a delimiting character such as an underline (_). This allows the fields to have a variable length as well as allowing for the omission of non-critical data field information.

Looking again at FIG. 11, the renaming software can be located at a provider computer. The renaming software will then prompt the user to input data into the required field, or the data which was previously input for different forms can be automatically input using the renaming software. In one embodiment, the receiving software 202 is the server which receives the renamed files and can route them using the data in the fields of the renamed file.

In an alternate embodiment of the present invention, the renaming software is at a web site on the server which has an Internet interface to the provider computer. The provider computer can input information to this web site as well as give an indication of the attachment. The client software at the provider renames the file, then transfer it to the server, or alternatively the files can be received with the original name and renamed at the server. The receiving software 202 can be located at the server or at a payer location.

FIG. 13 illustrates a web page for the attachment submission in one embodiment of the present invention. This embodiment shows the use of input fields, pull-down menus and the like to rename an attachment file.

Additional bill attachment embodiments also could be used. One embodiment identifies batches of files for routing not using a file name but producing an accompanying batch document that identifies the attachments. The batch document includes the necessary specifications for the delivery, linking and tracking of the attachment file. The file name for each attachment is a record in the batch document.

Another embodiment of the present invention is a system in which an accompanying document that identifies the file and provides the necessary specifications for the delivering, linking and tracking of the attachment documents. The file name for each attachment is a record in the file document. Each attachment is a single document with header information for purposes of delivery, linking and tracking.

Each of these alternate embodiments uses a separate element, such as a document or batch identifying information, to identify the attachments. The downside of these alternate embodiments is that it requires such additional elements. For these reasons, the use of the file name as the attachment file identifier is the preferred embodiment.

Figure 5:
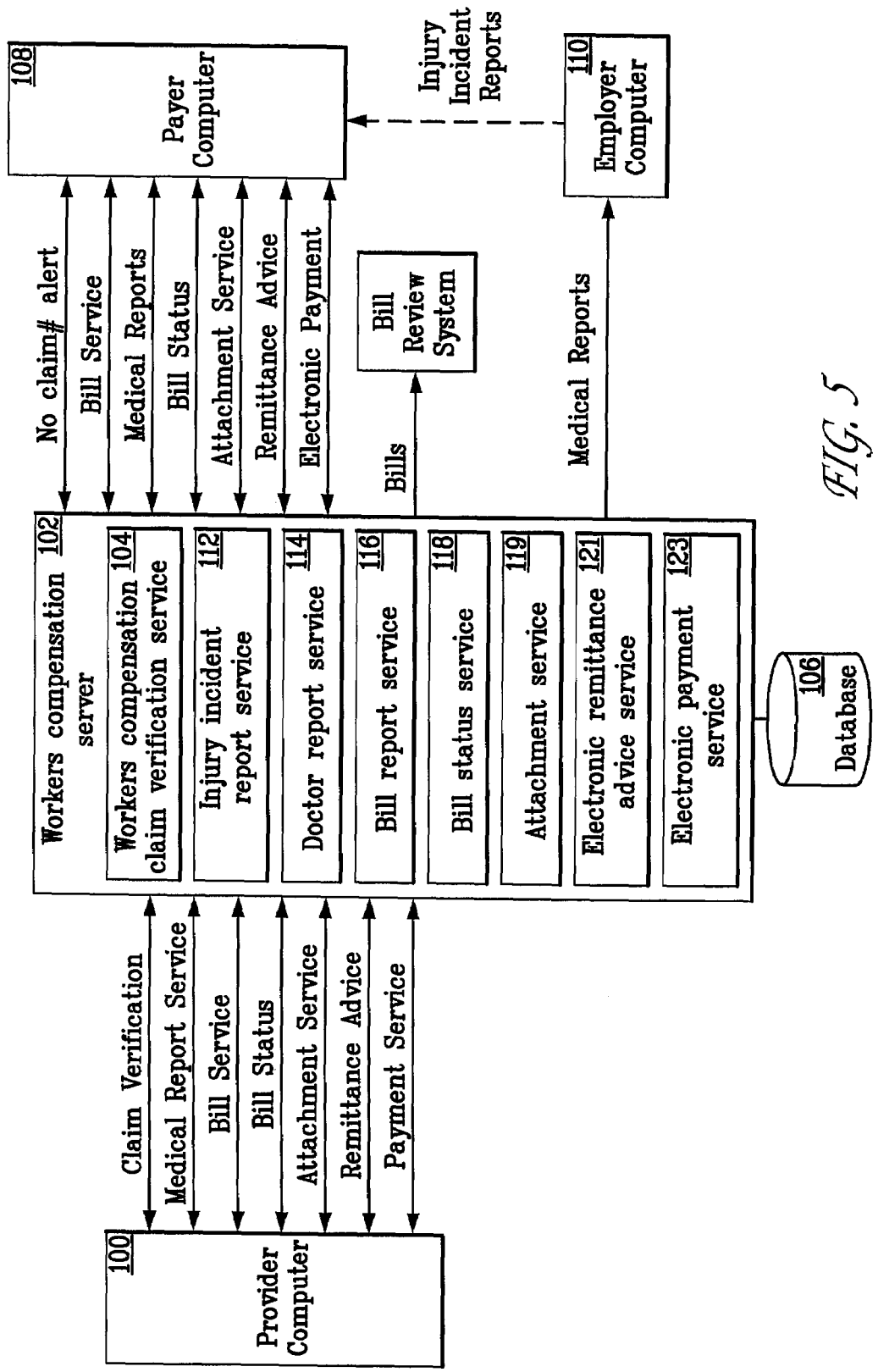
FIG. 5 is a diagram of a Workers' Compensation system in which software stored in the central Workers' Compensation server is accessed by a provider computer, a payer computer and an employer computer.

FIG. 5 illustrates an embodiment of the present invention in which a Workers' Compensation server is accessible across the Internet by a provider computer, payer computer, and employer computer. The Workers' Compensation server contains software accessible by the provider computer, payer computer, and employer computer across the Internet.

For example, the provider computer 100 accesses the Workers' Compensation server 102 across the Internet. If a claim verification service is to be used, the user at the provider computer accesses claim verification service software 104 at the Workers' Compensation server. This can be done after a log-in to identify the provider to the Workers' Compensation server. An electronic form is sent to the provider computer, allowing the provider to input a claim number request. The claim number request is sent to the Workers' Compensation server which checks the database 106. If a claim number is found, the indication of the claim number is sent to the provider computer 100. This indication can be a dynamically produced web page indicating the claim number. If no claim number is found, an E-mail notification can be sent to the payer computer as an alert. The E-mail notification alerts the payer that a claim number is needed. The provider is also notified that no claim number is found.

Payer computer 108 interacts with the employer computer 110 through the server as well. For example, the employer computer 110 has access to an injury incident report service 112. The provider computer 100 also has access to the doctor report service 114. The doctor report service 114 prompts the provider computer to input information sufficient for the doctor's first report of injury or illness. Such a report should include the employer, the date of injury and a description of the injury. This prompting is done such that the reports are sufficient for legal requirements in the specific locality. The formatted reports are sent to the payer computer 108 and employer computer 110. The provider computer 100 also has access to a bill report service 116. The bill report service allows the provider to input a bill, which is then sent to the correct recipient computer. This could be the payer computer 108 or, in an alternate embodiment, a bill review computer of a bill review service.

The attachment file service 119 is software that handles the association of attachment files with the bills. An example of the attachment file service is described with respect to FIGS. 11-13. The provider computer uses the bill status service software at the Workers' Compensation server 102 to automatically do a bill status check. The software at the Workers' Compensation server formats the user's inquiry and provides a report to the payer computer. This report could be, for example, an E-mail with a link to a dynamically created web page which allows the payer to select a reason why a certain bill has not been paid. Then a response report is sent to the provider computer 100 either through the Workers' Compensation server 110 or with an E-mail message.

Note that additional services can be provided by the Workers' Compensation server 102. The advantage of having the Workers' Compensation system software at the Workers' Compensation server is that it facilitates the system's use with multiple provider computers, payer computers and employer computers.

The Workers' Compensation server can also contain an electronic remittance advice service 121. Typically in the healthcare field, if a bill is not fully paid, the insurer will produce an explanation of benefits which will list, for each billed item, the reasons why not all of the charge has been paid. In one embodiment of the present invention, an electronic remittance advice service 121 is contained at the Workers' Compensation server 102. This electronic remittance advice service allows for a uniform system that payers can produce a standardized remittance advice input which can be then sent to the provider. The electronic remittance advice can be sent in electronic form to the provider computer 100. By providing the electronic remittance advice in electronic form, quick modification by the provider computer is made possible so that the electronic text of the explanation of benefits can be used to produce a supplemental bill. This supplemental bill is sent to a third party, or resent to the payer. The data in the electronic remittance advice simplifies the creation of such a supplemental bill. For example, if only half the fees for an X-Ray are paid and this information is contained in the electronic remittance advice, software at the provider computer can easily attempt to obtain the other half of the cost in a rebilling. In conventional systems, a hard copy of the explanation of benefits is sent and a keyboarder at the provider computer needs to retype the information based upon the explanation of benefits in order to produce any supplemental bill.

In one embodiment, an additional service provided by the Workers' Compensation server is an electronic payment service. When both the provider and the payer computer send signals indicating that the payment of the bill is desirable, the Workers' Compensation server sends a signal to a third party's electronic payment system such as those maintained by banks to automatically make the electronic payment between the payer system and the provider. By centralizing some of the electronic payment service at the server, the payer computer and provider computer need not interface with this third part payment system directly.

A number of subsystems can be implemented on the Workers' Compensation server. Reports can be preformatted and automated and drop-down menus provided. The data field can be linked to the database in a manner such that data input into the fields of the reports can be stored in the database 106 for data mining. For example the data input to the Workers' Compensation server can be stored in the database 106 associated with its field identifier. Thus, the primary diagnosis code data is associated with the identifier which is "primary diagnosis code." This allows the server to be a source of reports and other data-mining operations.

The Workers' Compensation server allows for storage, retrieval, and secure distribution of information. It also allows for the automated access to diagnosis treatment guidelines and prescription creation data. For example, if the diagnosis code is entered by the provider in a report, data can be sent from the Workers' Compensation server to indicate suggested treatments and suggested prescriptions. These guidelines can be either standardized guidelines or payer-suggested guidelines. Thus, if a provider inputs a report having a certain diagnosis code and a certain payer ID code, the payer's guidelines for that diagnosis code can be automatically sent to the provider.

FIGS. 6-10 illustrate the operations of one embodiment of the present invention.

FIG. 6 illustrates a web page which is accessed at the provider computer for inputting a doctor's first report of an occupational injury or illness. The report will prompt the user to include the necessary information required for each state's doctor's first report. This prompting can be done by the provider computer 100 accessing software stored at the Workers' Compensation server 102, or by the provider computer 110 downloading software from the Workers' Compensation server 102.

FIGS. 7A-7D illustrate a formatted doctor's report. The formatted doctor's report is produced by the system of one embodiment of the present invention and is automatically sent to the payer and employer computers based upon input provided by the provider at the provider computer for the doctor's first report of occupational injury or illness.

Figure 8C:
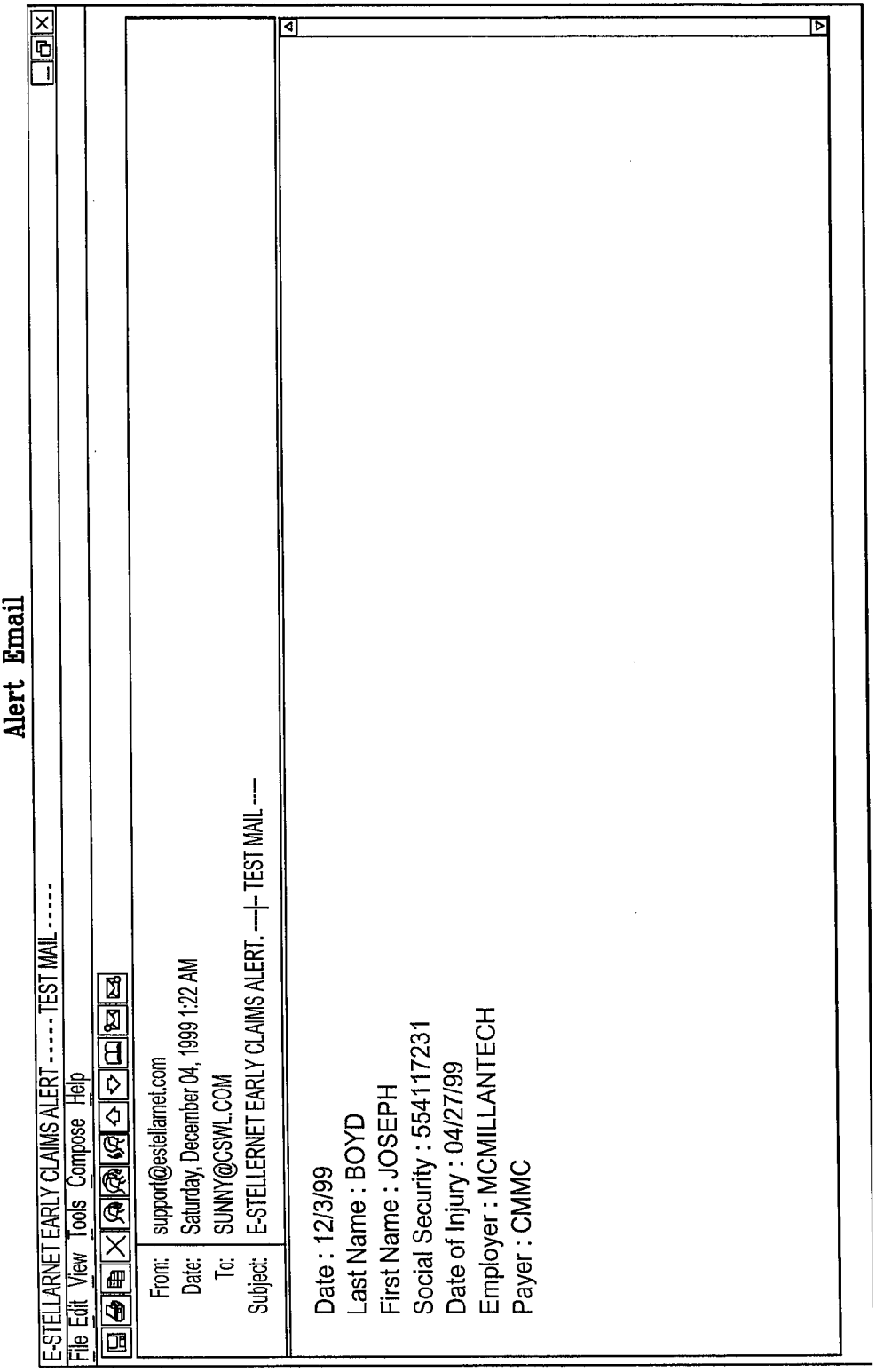
FIG. 8C shows an alert E-mail which is sent to a payer in the case that Workers' Compensation claims verification service cannot find a Workers' Compensation claim number.

FIG. 8A illustrates a Workers' Compensation claim verification service input electronic form which is provided to the provider computer. The provider accesses a web page which allows the input of information to identify a Workers' Compensation claim. The Workers' Compensation claim verification service then checks a database to determine the Workers' Compensation number corresponding to this claim. FIG. 8B illustrates the resulting web page based upon the input made by the provider. This result page includes the claim number which can be used by the provider in the bills and reports. FIG. 8C illustrates an alert E-mail which is sent by the Workers' Compensation server 102 to the payer computer to notify the payer of the potential problem due to lack of a Workers' Compensation number assigned to a claim.

Figure 9D:
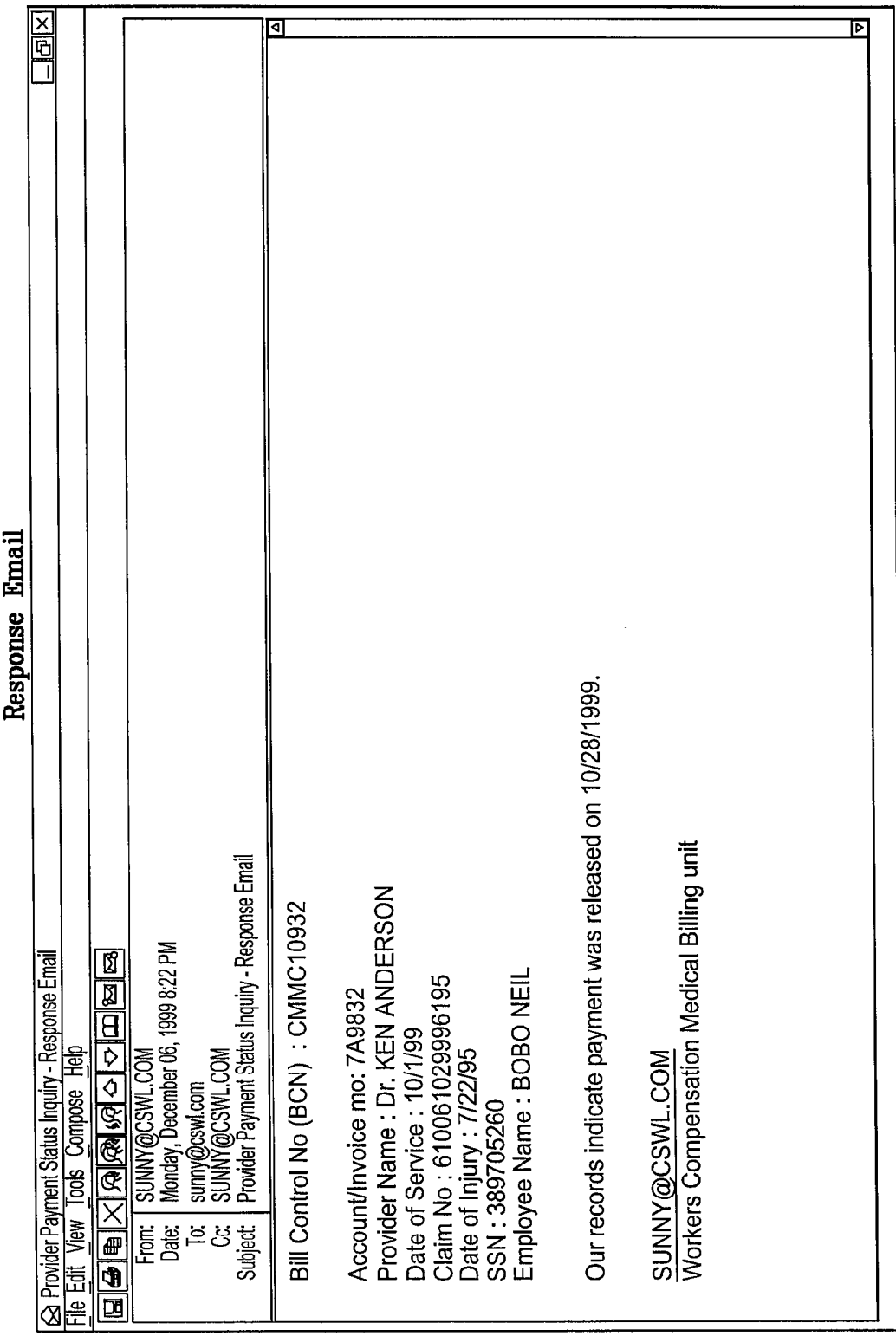
FIG. 9D is a response E-mail which is received by the provider in response to the payment inquiry.

FIG. 9A illustrates an inquiry form E-mail which is accessible by a provider computer 100 from a Workers' Compensation server 102. The system allows the user at the provider computer to input information identifying a bill and request a status for the bill. The Workers' Compensation server 102 then produces an E-mail as shown in FIG. 9B which is sent to the payer computer. In this embodiment, the received E-mail includes a link with a Universal Resource (URL) that instructs the Workers' Compensation server 102 to produce a dynamically created response form. The dynamically created response form allows the payer to input information concerning the status of the bill. In an alternate embodiment, the system can automatically search the payer computer database to determine the status of the bill. Once the payer inputs a response, a response E-mail is automatically created and sent to the provider computer.

Figure 10A:

FIGS. 10A and 10B illustrate sign-in pages for one example of a web page operating the Workers' Compensation server system of the present invention.

While the above is a complete description of the preferred embodiments of the present invention, various alternatives, modifications and equivalents can be used. It should be evident that the present invention is equally applicable by making appropriate modifications to the embodiment described above. For example, the Workers' Compensation software accessed by the provider computer and the software at the payer computer need not be physically located at the provider computer and payer computer, respectively. A distributed computing system, such as, computing across the Internet, could be used so that some or all of the calculations of the software are done at a remote server. Therefore, the above description should not be taken as limiting the scope of the invention, which is defined by the appended claims.

The invention claimed is:

1. A system for assisting providers to prepare billings associated with workers' compensation claims, comprising:
a workers' compensation claims verification system;
software accessed at a plurality of provider computers, the software prompting providers to input data concerning workers' compensation claims, and sending electronic claim number requests containing at least some of the inputted data across the Internet to the workers' compensation claim verification system;
wherein, the workers' compensation claims verification system
receives the data contained in the electronic claim number requests; and
determines whether matching workers' compensation claim numbers associated with the received data exist;
electronically supplies the matching workers' compensation claim numbers determined to exist to corresponding ones of the sending provider computers, wherein said providers use said supplied claim numbers to prepare the billings, and
automatically sends an indication of the lack of determining the workers' compensation claim number to at least one of a plurality of payer computers, each being associated with a different payer, for each matching workers' compensation claim number determined not to exist.

2. The system of claim 1 wherein the workers' compensation claims verification system further electronically requests a workers' compensation claim number from a selected one of said plurality of payer computers.

3. The system of claim 1 wherein the software accessed at the provider computer further uses the matching claim number received from the workers' compensation claim verification system to produce medical treatment reports.

4. The system of claim 1, wherein the workers' compensation claim verification system contains claim data for a number of payers.

5. The system of claim 1, wherein the workers' compensation claim verification system is updated with data obtained from said payer computers.

6. The system of claim 1, wherein said at least some of the data includes name data, social security data, and injury date data.

7. The system of claim 1, wherein the workers' compensation claim verification system comprises a database at a server.

8. The system of claim 7, wherein the workers' compensation claim verification system further:

receives at least one claim number from said payer computers; and matches the claim numbers with associated claim verification requests.

9. The system of claim 1, wherein the workers' compensation claim verification system further receives a plurality of unassigned claim numbers from said payer computers and assigns the unassigned claim numbers in response to claim verification requests received from provider computers.

10. The system of claim 1, wherein the workers' compensation claim verification system includes software that further allows each provider computer to access a payer computer, and each payer computer to access each provider computer.

11. The system of claim 1, wherein each payer is a different insurer.

12. The system of claim 11, wherein each sent indication alerts the associated insurer of a potential lack of claim incident information.

13. The system of claim 11, wherein each indication prompts the associated insurer to request claim incident information from an insured.

14. The system of claim 13, wherein each provider is a doctor having an associated patient having an associated employer, wherein the employer is the insured.

* * * * *